United States Patent [19]

Murray

[11] Patent Number: 5,720,964
[45] Date of Patent: Feb. 24, 1998

[54] HAIR CONDITIONING COMPOSITION

[75] Inventor: Andrew Malcom Murray, Cheshire, Great Britain

[73] Assignee: Chesebrough-Pond's USA Co., Division of Conopco, Inc., Greenwich, Conn.

[21] Appl. No.: 660,974

[22] Filed: Jun. 12, 1996

Related U.S. Application Data

[63] Continuation of Ser. No. 317,274, Oct. 4, 1994, abandoned.

[30] Foreign Application Priority Data

Oct. 6, 1993 [GB] United Kingdom ............... 9320556

[51] Int. Cl.$^6$ ............................. A61K 6/00; A61K 7/00
[52] U.S. Cl. ............................. 424/401; 424/70.12
[58] Field of Search ............................. 424/401, 70.12; 252/551, 174.15, 8.8

[56] References Cited

U.S. PATENT DOCUMENTS

| | | | |
|---|---|---|---|
| 2,891,920 | 6/1959 | Hyde et al. | 524/714 |
| 3,294,725 | 12/1966 | Findlay et al. | 524/745 |
| 3,360,491 | 12/1967 | Axon | 524/588 |
| 3,962,418 | 6/1976 | Birkofer | 424/70.19 |
| 4,009,256 | 2/1977 | Nowak, Jr. et al. | 424/70.16 |
| 4,874,416 | 10/1989 | Yokokawa et al. | 65/382 |
| 5,087,443 | 2/1992 | Chizat et al. | 424/47 |
| 5,114,706 | 5/1992 | Duvel | 424/70.17 |
| 5,198,209 | 3/1993 | Zhou et al. | 424/70.122 |
| 5,248,445 | 9/1993 | Rizvi et al. | 252/174.15 |
| 5,275,761 | 1/1994 | Bergmann | 252/551 |
| 5,306,434 | 4/1994 | Schueller et al. | 252/8.8 |
| 5,308,551 | 5/1994 | Beauquey et al. | 252/548 |
| 5,393,521 | 2/1995 | Lance-Gomez et al. | 424/70.12 |

FOREIGN PATENT DOCUMENTS

| | | |
|---|---|---|
| 0 268 982 | 6/1988 | European Pat. Off. . |
| 0 432 951 | 6/1991 | European Pat. Off. . |
| 0 463 780 | 1/1992 | European Pat. Off. . |
| 0 473 508 | 3/1992 | European Pat. Off. . |
| 0 529 883 | 3/1993 | European Pat. Off. . |
| WO 93/08787 | 5/1993 | WIPO . |

OTHER PUBLICATIONS

Halloran, Daniel J., "A Silicone Selection Guide for Developing Conditioning Shampoos", In Soap, Cosmetics, Chemical Specialties, vol.68, No. 3, pp. 22–26, published Mar. 1992.

Wendel, Samuel R. et al., "Organofunctional Silicones for Personal Care Application", Cosmetics & Toiletries, vol. 98, May 1988, pp. 103–106.

Great Britain Search Reports in Great Britain Patent Application No. 9320556.5.

*Primary Examiner*—Thurman K. Page
*Assistant Examiner*—William E. Benston, Jr.
*Attorney, Agent, or Firm*—Rimma Mitelman

[57] ABSTRACT

A hair conditioning shampoo composition containing (a) about 2 to about 50% by weight of anionic surfactant, (b) about 50 to about 98% by weight water; (c) 0.01 to 10% by weight of an emulsion polymerized dimethiconol nonionic conditioning polymer, (d) 0.01 to 5% by weight of a cationic deposition polymer having a charge density between 0.1 and 4 meq/g, and (e) water.

10 Claims, No Drawings

HAIR CONDITIONING COMPOSITION

This is a continuation of Ser. No. 08/317,274, filed Oct. 4, 1994, now abandoned.

This invention relates to hair conditioning compositions containing non-volatile insoluble silicone gum, particularly dimethiconol gum.

Use of high viscosity gums as hair conditioning agents is known and suitable gums are described in U.S. Pat. No. 4,874,416 (Spitzer). The gums are usually used in solution in a volatile silicone such as a cyclomethicone.

Emulsion polymerised silicones are known from U.S. Pat. No. 2,891,920 (Hyde), U.S. Pat. No. 3,294,725 (Findlay), and U.S. Pat. No. 3 360 491 (Axon).

Emulsion polymerised dimethylpolysiloxane microemulsions are described in EP 0 268 982 (Toray). Dimethiconol materials are taught as one of a range of possibilities. Table 7 shows shampoo compositions which use emulsion polymerised silicones. Emulsion A, a trimethylsiloxy terminated dimethylpolysiloxane with a degree of polymerization of 100 (molecular weight calculated at 7 500) is used with Merquat 550, a cationic polymer. Emulsion C, which was a hydroxy-terminated dimethyl polysiloxane having a degree of polymerisation of 1200 (molecular weight approximately 90 000), was used alone.

Articles such as "Organofunctional Silicones for Personal Care Applications", Wendel, Samuel R and DiSapio, Alfred J. *Cosmetics & Toiletries* vol 98 May 1983, pp 103–106 have taught away from the use of Dimethiconol in hair compositions. Dimethiconol can be prepared in various ways, one of which is emulsion polymerisation.

Silicone oils are often added to hair conditioning compositions in the form of aqueous emulsions. These emulsions are usually formed by mechanical shearing of the oil. Sometimes they are formed by chemical emulsification but this is not the same as emulsion polymerisation and does not provide the unexpected advantages of the present invention.

A problem with prior hair conditioning compositions has been that they either provide inadequate conditioning, particularly when anionic surfactant is also present in a so called "2 in 1 shampoo"; or the use of high viscosity gums leads to processing difficulties. The latter problem has in the past been partially solved by the use of solvent for the gum. Such solvents are undesirable for the consumer and affect the conditioning properties of the gum.

According to the present invention a hair conditioning shampoo composition comprises:
(a) about 2 to about 50% by weight of anionic surfactant,
(b) about 50 to about 98% by weight water,
(c) 0.01 to 10% by weight of an emulsion polymerised dimethiconol nonionic conditioning polymer having the formula:

where n is 2700 or more to give a molecular weight of over 200 000, and
(d) 0.01 to 5% by weight of a cationic deposition polymer having a cationic charge density of from 0.1 to about 4 meq/g.

A water soluble, cationic deposition polymer is an essential element of the present invention. It will generally be present at levels of from 0.01 to 5%, preferably from about 0.5 to 1%, more preferably from about 0.08% to about 0.5% by weight. The polymer may be a homopolymer or be formed from two or more types of monomers. The molecular weight of the polymer will generally be between 5 000 and 10 000 000, typically at least 10 000 and preferably in the range 100 000 to about 2 000 000. The cationic polymers will have cationic nitrogen containing groups such as quaternary ammonium or protonated amino groups, or a mixture thereof.

The cationic charge density has been found to need to be at least 0.1 meq/g, preferably above 0.8 or higher. The cationic charge density should not exceed 4 meq/g, it is preferably less than 3 and more preferably less than 2 meq/g. The charge density can be measured using the Kjeldahl method and should be within the above limits at the desired pH of use, which will in general be from about 3 to 9 and preferably between 4 and 8.

The cationic nitrogen-containing group will generally be present as a substituent on a fraction of the total monomer units of the cationic polymer. Thus when the cationic polymer is not a homopolymer it can contain spacer non-cationic monomer units. Such polymers are described in the CTFA Cosmetic Ingredient Directory, 3rd edition.

Suitable cationic polymers include, for example, copolymers of vinyl monomers having cationic amine or quaternary ammonium functionalities with water soluble spacer monomers such as (meth)acrylamide, alkyl and dialkyl (meth)acrylamides, alkyl (meth)acrylate, vinyl caprolactone and vinyl pyrrolidine. The alkyl and dialkyl substituted monomers preferably have C1–C7 alkyl groups, more preferably C1–3 alkyl groups. Other suitable spacers include vinyl esters, vinyl alcohol, maleic anhydride, propylene glycol and ethylene glycol.

The cationic amines can be primary, secondary or tertiary amines, depending upon the particular species and the pH of the shampoo. In general secondary and tertiary amines, especially tertiary, are preferred.

Amine substituted vinyl monomers and amines can be polymerized in the amine form and then converted to ammonium by quaternization.

Suitable cationic amino and quaternary ammonium monomers include, for example, vinyl compounds substituted with dialkyl aminoalkyl acrylate, dialkylamino alkylmethacrylate, monoalkylaminoalkyl acrylate, monoalkylaminoalkyl methacrylate, trialkyl methacryloxyalkyl ammonium salt, trialkyl acryloxyalkyl ammonium salt, diallyl quaternary ammonium salts, and vinyl quaternary ammonium monomers having cyclic cationic nitrogen-containing rings such as pyridinium, imidazolium, and quaternized pyrrolidine, e.g., alkyl vinyl imidazolium, and quaternized pyrrolidine, e.g., alkyl vinyl imidazolium, alkyl vinyl pyridinium, alkyl vinyl pyrrolidine salts. The alkyl portions of these, monomers are preferably lower alkyls such as the $C_1$–$C_3$, alkyls, more preferably $C_1$ and $C_2$ alkyls.

Suitable amine-substituted vinyl monomers for use herein include dialkylaminoalkyl acrylate, dialkylaminoalkyl methacrylate, dialkylaminoalkyl acrylamide, and dialkylaminoalkyl methacrylamide, wherein the alkyl groups are preferably $C_1$–$C_7$ hydrocarbyls, more preferably $C_1$–$C_3$, alkyls.

The cationic polymers hereof can comprise mixtures of monomer units derived from amine- and/or quaternary ammonium-substituted monomer and/or compatible spacer monomers.

Suitable cationic hair conditioning polymers include, for example: copolymers of 1-vinyl-2-pyrrolidine and 1-vinyl-3-methyl-imidazolium salt (e.g., Chloride salt) (referred to in the industry by the Cosmetic, Toiletry, and Fragrance Association, "CTFA", as Polyquaternium-16) such as those commercially available from BASF Wyandotte Corp. (Parsippany, N.J., USA) under the LUVIQUAT tradename (e.g., LUVIQUAT FC 370); copolymers of 1-vinyl-2- pyrrolidine and dimethylaminoethyl methacrylate (referred to in the industry by CTFA as Polyquaternium-11) such as those commercially from Gar Corporation (Wayne, N.J., USA) under the GAFQUAT tradename (e.g., GAFQUAT 755N); cationic diallyl quaternary ammonium-containing polymers, including, for example, dimethyldiallyammonium chloride homopolymer and copolymers of acrylamide and dimethyldiallyammonium chloride, referred to in the industry (CTFA) as Polyquaternium 6 and Polyquaternium 7, respectively; and mineral acid salts of amino-alkyl esters of homo-and co-polymers of unsaturated carboxylic acids having from 3 to 5 carbon atoms, as described in U.S. Pat. No. 4,009,256, incorporated herein by reference.

Other cationic polymers that can be used include polysaccharide polymers, such as cationic cellulose derivatives and cationic starch derivatives.

Cationic polysaccharide polymer materials suitable for use herein include those of the formula:

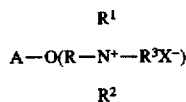

wherein: A is an anhydroglucose residual group, such as starch or cellulose anhydroglucose residual, R is an alkylene oxyalklene, polyoxyalkylene, or hydroxyalkylene group, or combination thereof, $R^1$, $R^2$ and $R^3$ independently are alkyl, aryl, alkylaryl, arylalkyl, alkoxyalkyl, or alkoxyaryl groups, each group containing up to about 18 carbon atoms, and the total number of carbon atoms for each cationic moiety (i.e., the sum of carbon atoms in $R^1$, $R^2$ and $R^3$) preferably being about 20 or less, and X is an anionic counterion , as previously described.

Cationic cellulose is available from Amerchol Corp. (Edison, N.J., USA) in their Polymer JR (trade mark) and LR (trade mark) series of polymers, as salts of hydroxyethyl cellulose reacted with trimethyl ammonium substituted epoxide, referred to in the industry (CTFA) as Polyquaternium 10. Another type of cationic cellulose includes the polymeric quaternary ammonium salts of hydroxyethyl cellulose reacted with lauryl dimethyl ammonium-substituted epoxide, referred to in the industry (CTFA) as Polyquaternium 24. These materials are available from Amerchol Corp. (Edison, N.J., USA) under the tradename Polymer LM-200.

Other cationic polymers that can be used include cationic guar gum derivatives, such as guar hydroxypropyltrimonium chloride (Commercially available from Celanese Corp. in their Jaguar trademark series). Other materials include quaternary nitrogen-containing cellulose ethers (e.g. as described in U.S. Pat. No. 3,962,418, incorporated by reference herein), and copolymers of etherified cellulose and starch (e.g., as described in U.S. Pat. No. 3,958,581, incorporated by reference herein).

As discussed above, the cationic polymer hereof is water soluble. This does not mean, however, that it must be soluble in the shampoo composition. Preferably, however, the cationic polymer is either soluble in the shampoo composition, or in a complex coacervate phase in the shampoo composition formed by the cationic polymer and anionic material. Complex coacervates of the cationic polymer can be formed with anionic surfactants or with anionic polymers that can optionally be added to the compositions hereof (e.g., sodium polystyrene sulfonate).

Coacervate formation is dependent upon a variety of criteria such as molecular weight, concentration, and ratio of interacting ionic materials, ionic strength (including modification of ionic strength, for example, by addition of salts), charge density of the cationic and anionic species, pH, and temperature.

It is believed to be particularly advantageous for the cationic polymer to be present in the shampoo in a coacervate phase, or to form a coacervate phase upon application or rinsing of the shampoo to or from the hair. Complex coacervates are believed to more readily deposit on the hair. Thus, in general, it is preferred that the cationic polymer exist in the shampoo as a coacervate phase or form a coacervate phase upon dilution. If not already a coacervate in the shampoo, the cationic polymer will preferably exist in a complex coacervate form in the shampoo upon dilution with water to a water:shampoo composition rate ration of about 20:1, more preferably at about 10:1, even more preferably at about 8:1.

Techniques for analysis of formation of complex coacervates are known in the art. For example, microscopic analyses of the shampoo compositions, at any chosen stage of dilution, can be utilized to identify whether a coacervate phase has formed. Such coacervate phase will be identifiable as an additional emulsified phase in the composition. The use of dyes can aid in distinguishing the coacervate phase from other insoluble phases dispersed in the composition.

Preferably the deposition polymer is selected from the group comprising hydroxyalkyl cellulose ethers and cationic guar derivatives. Particularly preferred deposition polymers are Jaguar C13S with a cationic charge density of 0.8meq/g. Other particularly suitable materials include Jaguar C15, Jaguar C17 and Jaguar C16 and Jaguar C162, A preferred cellulose ether is Polymer JR400.

Preferably the average particle size of the dimethiconol polymer is less than 20 microns and more preferably it is less than 2 microns. Small particle size enables a more uniform distribution of silicone conditioning agent on the hair for the same concentration of silicone in the shampoo. The polymer can be cross-linked.

The composition may further comprises from 0.1 to 5% of a silicone suspending agent selected from selected from polyacrylic acids cross linked polymers of acrylic acid, copolymers of acrylic acid with a hydrophobic monomer, copolymers of carboxylic acid- containing monomers and acrylic esters, cross-linked copolymers of acrylic acid and acrylate esters, heteropolysaccharide gums and crystalline long chain acyl derivatives. The long chain acyl derivative is desirably selected from ethylene glycol stearate, alkanolamides of fatty acids having from 16 to 22 carbon atoms and mixtures thereof. Ethylene glycol distearate and Polyethylene glycol 3 distearate are preferred long chain acyl derivatives. Polyacrylic acid is available commercially as Carbopol 420, Carbopol 488 or Carbopol 493. Polymers of acrylic acid cross-linked with a polyfunctional agent may also be used, they are available commercially as Carbopol 910, Carbopol 934, Carbopol 940, Carbopol 941 and Carbopol 980. An example of a suitable copolymer of a carboxylic acid containing a monomer and acrylic acid esters is Carbopol 1342. All Carbopol materials are available from Goodrich and Carbopol is a trade mark.

Suitable cross linked polymers of acrylic acid and acrylate esters are Pemulen TR1 or Pemulen TR2. A suitable heteropolysaccharide gum is xanthan gum, for example that available as Kelzan mu.

Advantageously the viscosity of the dimethiconol lies in the range 1–20 million cst because higher viscosity increases the conditioning effect obtainable from the silicone.

The shampoo also contains anionic surfactant together with optional nonionic and amphoteric surfactant.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha-olefin sulphonates, especially their sodium, magnesium, ammonium and mono-, di- and triethanolamine salts. The alkyl groups generally containing from 8 to 18 carbon atoms and may be unsaturated. The alkyl ether sulphates, alkyl ether phosphates and alkyl ether carboxylates may contain from one to 10 ethylene oxide or propylene oxide unites per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2EO and 3EO, ammonium lauryl sulphate and ammonium lauryl ether sulphate 1EO, 2EO and 3EO.

The nonionic surfactants suitable for use in the composition of the invention may include condensation products of aliphatic ($C_8$–$C_{18}$) primary or secondary linear or branched chain alcohols or phenols with alkylene oxides, usually ethylene oxide and generally 6–30 EO.

Other suitable nonionics include mono or di alkyl alkanolamides or alkyl polyglucosides. Examples include coco mono or diethanolamide, coco mono isopropanolamide, and coco di glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutameates wherein the alkyl and acyl groups have from 8 to 18 carbon atoms. Examples include lauryl amine oxide, cocodimethyl sulphopropyl betaine and preferably lauryl betaine, cocamidopropyl betaine and sodium cocamphopropionate.

The surfactants are present in the shampoo composition of the invention in an amount of from 2 to 40% by weight, and preferably from 5 to 30% by weight.

The shampoo may also include minor amounts of other ingredients such as antibacterial agents, foam boosters, pearlescers, perfumes, dyes, colouring agents, preservatives, thickeners, proteins, polymers, phosphate esters and buffering agents The invention also comprises a method for preparation of a conditioning shampoo which contains insoluble silicone having a molecular weight above 200 000 and a viscosity of greater than 1 million cst as the conditioning agent comprising the steps of forming the silicone into an emulsion, the emulsion having a viscosity of less than 1000 cps, then mixing the emulsion with the other shampoo ingredients. Preferably the emulsion comprises greater than 50% by weight of the silicone.

In a preferred method the silicone is emulsion polymerised because such a material is able to combine small particle size with high viscosity.

Dimethiconol silicone is particularly preferred. The dimethiconol silicone can either be used as such or it can be end-capped with a further methyl group.

The invention will now be further described with reference to the following examples:

|  | EXAMPLE# | | | |
|---|---|---|---|---|
|  | 1 % | 2 % | 3 % | A % |
| SLES 2 EO[1] | 16 | 16 | — | 16 |
| SLES 3 EO[2] | — | — | 8 | — |
| CAPB[3] | 2 | 2 | 4 | 2 |
| Deposition polymer[4] | 0.1 | — | — | 0.1 |
| Deposition polymer[5] | — | 0.1 | — | — |
| deposition polymer[6] | — | — | 0.3 | — |
| X2-1766[7] | 3.2 | — | 5.0 | — |
| X2-1784[8] | — | 3.0 | — | — |
| BY-22-026[9] | — | — | — | 4.0 |
| EGDS[10] | 1.5 | — | — | 1.5 |
| Carbopol 980 | — | 0.4 | 0.4 | |
| water | to 100% | | | |

[1] is Sodium lauryl ether sulphate with 2 mols of ethoxylation
[2] is Sodium lauryl ether sulphate with 3 mols of ethoxylation
[3] is coco amidopropyl betaine
[4] is Jaguar C-13-S
[5] is Jaguar C-17
[6] is Polymer JR 400
[7] is a 60% silicone emulsion polymer, mol wt 300,000
[8] is a 50% silicone emulsion polymer, mol wt 240,000
[9] is a 50% mechanical emulsion of silicone, mol wt 115,000
[10] is ethylene glycol distearate Examples 1 and A were compared with a control silicone based conditioning shampoo sold in the UK under the trade name "WASH and GO for dry/sensitive hair". The compositions were used to treat identical hair switches which were then subjected to a series of paired comparison tests by trained panellists. The two attributes considered to be most indicative of conditioning benefit are (a) ease of dry combing and (b) smooth feel of the hair when dry.

Comparative example A was found to be equivalent to the control in both tests. Example 1 was found to be superior to the control in both tests.

This shows that the emulsion polymerized dimethiconol material of example 1 has superior hair conditioning properties to the mechanically emulsified silicone of comparative example A.

Examples 2 and 3 also gave excellent conditioning when tested on human hair.

I claim:

1. A hair conditioning shampoo composition comprising:
   (a) about 2 to about 50% by weight of anionic surfactant, (b) about 50 to about 98% by weight water, (c) 0.01 to 10% by weight of an emulsion polymerised dimethiconol nonionic conditioning polymer having the formula:

where n is greater than 2700, and (d) 0.01 to 5% by weight of a cationic deposition polymer having a charge density between 0.1 and 4 meq/g, and (e) water.

2. A composition according to claim 1 wherein the average particle size of the dimethiconol polymer is less than 20 microns.

3. A composition according to claim 2 wherein the average particle size of the dimethiconol polymer is less than 2 microns.

4. A composition according to claim 1 which further comprises from 0.1 to 5% of a silicone suspending agent selected from selected from "carbopol" and long chain acyl derivatives in the form of crystals.

5. A composition according to claim 1 wherein the viscosity of the dimethiconol lies in the range 1–20 million cst.

6. A composition according to claim 1 wherein the cationic deposition polymer is selected from the group comprising hydroxyalkyl cellulose ethers and cationic guar derivatives.

7. A method for preparation of a conditioning shampoo which contains insoluble silicone having a molecular weight above 200 000 and a viscosity of greater than 1 million cst as the conditioning agent comprising the steps of forming the silicone into an emulsion, the emulsion having a viscosity of less than 1000cps, then mixing the emulsion with the other shampoo ingredients.

8. A method as claimed in claim 7 wherein the emulsion comprises more than 50% by weight of the silicone.

9. A method as claimed in claim 7 wherein the silicone is emulsion polymerised.

10. A method according to claim 7, wherein the silicone is dimethiconol.

* * * * *